United States Patent
Pond

(10) Patent No.: US 10,098,708 B2
(45) Date of Patent: Oct. 16, 2018

(54) ULTRASONIC DEVICE HAVING MEMORY CAPABILITIES

(75) Inventor: Gary J. Pond, Milwaukee, WI (US)

(73) Assignee: INTER-MED, INC., Racine, WI (US)

( * ) Notice: Subject to any disclaimer, the term of this patent is extended or adjusted under 35 U.S.C. 154(b) by 0 days.

(21) Appl. No.: 12/799,736

(22) Filed: Apr. 30, 2010

(65) Prior Publication Data

US 2011/0087605 A1    Apr. 14, 2011

Related U.S. Application Data

(60) Provisional application No. 61/214,961, filed on Apr. 30, 2009.

(51) Int. Cl.
- *A61B 17/24* (2006.01)
- *A61C 3/03* (2006.01)
- *G06Q 30/00* (2012.01)

(52) U.S. Cl.
CPC ............. *A61C 3/03* (2013.01); *G06Q 30/012* (2013.01)

(58) Field of Classification Search
USPC .................................. 606/162, 169, 196, 180
See application file for complete search history.

(56) References Cited

U.S. PATENT DOCUMENTS

| | | | |
|---|---|---|---|
| 5,425,375 A * | 6/1995 | Chin et al. ..................... 600/549 |
| 2003/0013948 A1* | 1/2003 | Russell .............. A61B 5/04282 600/372 |
| 2007/0247768 A1* | 10/2007 | Meehleder et al. ............ 361/42 |
| 2008/0044790 A1* | 2/2008 | Fani ..................... A61C 1/0015 433/119 |
| 2008/0293008 A1* | 11/2008 | Regere et al. ................. 433/119 |
| 2009/0047624 A1* | 2/2009 | Tsai ............................... 433/119 |
| 2009/0065565 A1* | 3/2009 | Cao .................... A61B 18/1402 235/375 |
| 2009/0157094 A1* | 6/2009 | Yeshurun et al. ............. 606/131 |
| 2010/0030136 A1* | 2/2010 | Dacquay et al. ............... 604/65 |
| 2010/0036535 A1* | 2/2010 | Feine .................... A61C 1/0061 700/282 |

* cited by examiner

*Primary Examiner* — Kira Nguyen
(74) *Attorney, Agent, or Firm* — Quarles & Brady LLP

(57) ABSTRACT

A dental device capable of monitoring at least one characteristic of the dental device. The characteristics are monitored by the use of microchips; radio frequency identification devices (RFID), bar codes, resistors, diodes, semiconductors, and magnetic strips.

12 Claims, 3 Drawing Sheets

ULTRASONIC DEVICE HAVING MEMORY CAPABILITIES

RELATED APPLICATIONS

This application claims the benefit U.S. Provisional Patent Application Ser. No. 61/214,961, filed 30 Apr. 2009.

BACKGROUND OF THE INVENTION

The present invention relates to ultrasonic dental tools, and, more specifically, to ultrasonic dental tools that incorporate devices that can record and store operational information of the ultrasonic dental tool.

Ultrasonic devices are commonly used in dental procedures, such as root canal procedures, scaling and cleaning procedures, and other various dental procedures. These devices generally comprise a handpiece connected to a dental tip or other similar attachment. The handpiece will generally be connected to a power source and/or housing, and one or more fluid sources. There are two distinct types of ultrasonic devices, magnetorestrictive and piezoelectric ultrasonic devices.

Magnetorestrictive devices are designed to hold a dental insert within the body of the device. The dental insert is placed within the handpiece and connects with a power source to provide ultrasonic vibration for the device. The dental insert can wear over time and may need to be replaced. Depending on the specific use for the ultrasonic device and the specific dental attachment used, the power amplitude of the ultrasonic device may need to be changed—improper setting of the power amplitude may prematurely wear out the ultrasonic dental tip. Systems have been developed to assist a person in monitoring the use of these devices. An example can be found in Fani et al. U.S. Pat. Appl. 2008/0044790.

Piezoelectric devices provide ultrasonic energy to a dental tip connected to a handpiece. An oscillating ultrasonic member located within the handpiece will be connected to the dental tip, which can then vibrate and deliver the necessary ultrasonic energy to a dental work area, such as a root canal.

Such piezoelectric devices do not require an insert as do magnetorestrictive devices. However, during general use, the dental tips themselves may become fatigued. For example, a typical dental tip may be driven at a predetermined amplitude and be required to operate for a significant amount of time (i.e. 100 hours). The dental tips for these devices may wear over time, regardless of how the dental tip has been used. Nonetheless, due to the relatively smaller size and configuration of these devices compared to magnetorestrictive devices, it has not been possible to monitor the characteristics of these devices effectively, as with magnetorestrictive devices. Consequently, determining specifically how and why a dental tip failed is not always possible.

SUMMARY OF THE INVENTION

The present invention discloses an ultrasonic dental device and/or a dental tip that has the capability to store and record information for operational convenience or manufacturer warranty purposes within the dental device or dental tip. The dental device generally comprises a housing with a dental tool attached to the housing. The dental tool is preferably an ultrasonic dental tool.

The present invention provides systems and methods for monitoring the characteristics of ultrasonic dental devices, most preferably piezoelectric devices.

The system generally comprises a dental tip that has a monitoring device located within the dental tip. The dental tip would be connected to an ultrasonic handpiece, which is connected to a base assembly, that comprises a power source and other controls and control functions.

The monitoring device can be a microchip that can be attached and removed from the dental tip when necessary. The microchip may be analyzed to determine whether or not the dental tip was properly used and what were the circumstances that led to the failure of the dental tip. Other monitoring devices may be used in the system, such as radio frequency identification devices (RFID), bar codes, resistors, diodes, semiconductors, magnetic strips, or Hall Effect sensors.

Likewise the monitoring device could be located within the ultrasonic device, such as within the housing, base station or within the dental tool, i.e. handpiece.

The process of monitoring the characteristics could take place directly on the dental tip via a microchip, or conversely, the monitoring characteristics could take place in the dental handpiece or the base assembly. Appropriate data could then be recorded and stored directly on the dental tip or likewise could be transmitted to the tip from the handpiece or base assembly. Additionally, the data could be collected from the dental tip, handpiece or base assembly and written to various forms of storage media (i.e. SD flash memory, USB drive, Ethernet, etc.) to later be analyzed by the manufacturer to determine usage characteristics.

Additionally, it is also possible that the dental tool or base station may interface with elements in the dental tip. For example, if a tip were identified by the base station and the tip were operated outside of its recommended operating parameters, then the base station could send an electronic signal to the tip to overload an electronic device. The failure of the small electronic device would provide a parameter which would then be easy for a manufacturer to evaluate upon receipt of the returned tip. Thus in this example, a manufacturer would be able to easily obtain data about the usage of a particular dental tip to support warranty claims.

In one aspect, the dental tip could include an electronic device, such as a diode, transistor, resistor, piezoelectric crystal, op-amp, fuse, circuit breaker or other safety protection or monitoring device. The safety protection or monitoring device contained in or on the dental tip would be in communication with either the dental tool or base station, or both. The safety protection or monitoring device could then be used to determine user compliance, as the device would serve as a means to determine whether the dental tip was operated outside of its recommended limit in terms of amplitude, frequency or fatigue cycles.

In one embodiment, noncompliance could be determined by causing the safety protection device to fail. Failure could be produced by exceeding the operational specifications of the safety protection device, for example by exceeding a given voltage or ampere rating, or otherwise known as overloading the safety protection device. In one exemplary instance, the safety protection device would be overloaded if the operator used the dental tip at higher amplitudes than defined by the manufacturer.

Specifically, the base station could continually transmit an electrical characteristic to the safety protection or monitoring device, however once the amplitude level of the dental tip was increased beyond the rated usage, the electrical characteristic from the base station would overload the safety protection or monitoring device. Upon review of the dental tip, the manufacturer would be able to determine that the tip was used under conditions not recommended since the safety protection device had failed. This could be determined as easily as measuring the resistance across the safety protection device, and would allow the manufacturer to either void or honor the warranty of the dental tip.

In another embodiment, the dental tip may contain a package of passive elements structured in an array with differing mechanical stress, strain and fatigue properties. This array of passive elements may also have variable electrical properties which are variable with mechanical plastic deformation of the elements. The elements could be composed of any combination of diodes, transistors, resistors, piezoelectric crystals, various kinds of semiconductor junctions, or other ohmic or non-ohmic devices. These elements could be placed on a single integrated circuit chip, if desired. Elements in the array would then demonstrate variable mechanical and electrical properties.

For example, if a tip experienced accelerations indicative of it being used beyond its recommended power range, an element(s) could fail. Then, when the user returned the tip to the manufacturer, the manufacturer could verify that this tip was operated outside of its recommended operating parameters. The verification could involve interfacing with said integrated circuit chip to determine that it was used outside of its recommended operating parameters by measuring electronic parameters, such as evaluating internal connections or evaluating current-voltage (I-V) curves.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
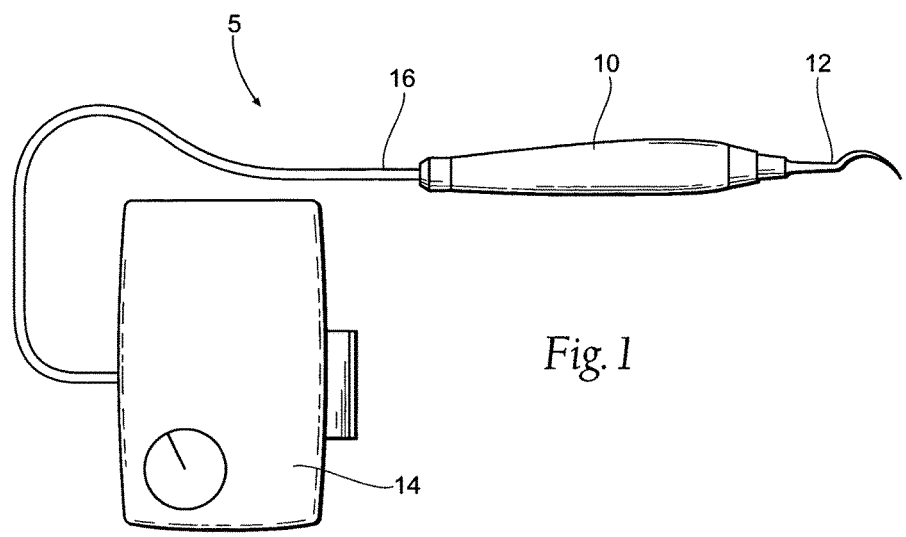
FIG. 1 is a plan view of an ultrasonic dental device to be used in accordance with the present invention.

FIG. 1 depicts a dental assembly 5 that generally comprises a dental handpiece 10 and a dental needle or tip 12 connected to the handpiece 10. The handpiece 10 is connected to a base station 14 by way of a power cord 16. It is also possible that the handpiece 10 could be connected to the base station via a wireless arrangement. The base station 14 generally comprises various controls and control functions for the handpiece 10 and the dental tip 12, such as providing a power source, providing temperature controls, providing controls for the speed and frequency for the operation of the handpiece 10 and the tip 12, and other controls functions as are necessary for operating the dental assembly 5.

Figure 2:
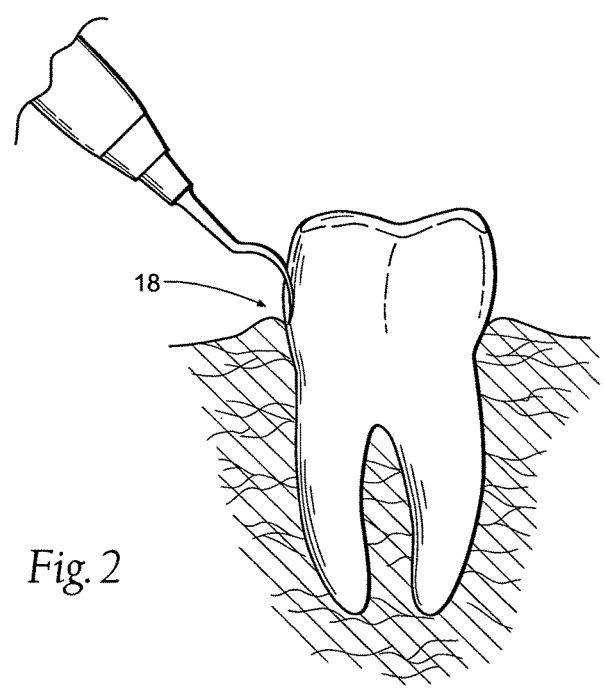
FIG. 2 is a plan view of the ultrasonic device shown in FIG. 1, further shown being used near a tooth.

The dental assembly 5 is an ultrasonic dental tool, with the dental handpiece 10 being an ultrasonic dental handpiece, and, more particularly, being a piezoelectric ultrasonic handpiece. The handpiece 10 provides the necessary vibration and oscillation for the dental tip 12 to provide ultrasonic energy to a dental area 18, as shown in FIG. 2. FIG. 2 depicts the dental tip 12 as a scaler or scaling device, but other dental tools, such as drills or other dental tools used for endodontic procedures could be used as the dental tool receiving ultrasonic energy. The dental assembly 5 may also be capable of particularly identifying what type of dental tip is attached to the handpiece. This could be done in a variety of fashions, such as electronic, magnetic, optical, mechanical or RF wireless means.

Ultrasonic tools and devices have been used in a variety of ways and in a variety of settings, from clinical and professional uses to individual uses for toothbrushes and other personal hygiene devices. Use of dental tools has also expanded into various regions and areas around the world, especially since devices have become more cost effective and more portable. Consequently, a variety of users having varying levels of operating skills can lead to improper uses of the devices, such as operating the dental device and tip at the wrong power amplitude or speed, applying too much pressure or force to the dental tip, or operating the device for too long of a period of time. Any combination of variables can lead to increased wear or premature failure of the dental tip 12 being used.

Figure 3:
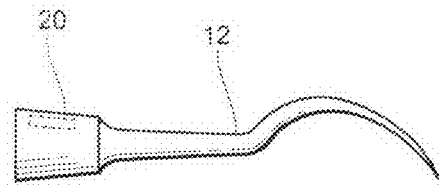
FIG. 3 is a perspective view of an ultrasonic dental tip used according to the present invention, demonstrating a monitoring device within the dental tip.

FIG. 3 demonstrates the dental tip 12 arranged according to the present invention. The dental tip further comprises monitoring means 20, which can be in the form of a microchip, a radio frequency identification device (RFID), or another device, such as resistors, diodes, semiconductors, or magnetic strips, or another arrangement that is sized and suited to be inserted into or work together within the small area of the dental tip 12, without interfering with the functioning of the dental tip 12. The monitoring means 20 could be used to monitor the use of the dental tip 12 as it is being used and, also, to store information on how the dental tip 12 was being used so that the dental tip 12 could be evaluated at another place or time.

Figure 4:
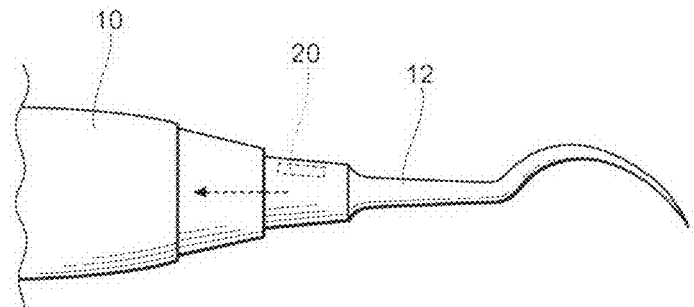
FIG. 4 is a partial perspective view of the dental tip of FIG. 3 and a dental handpiece according to the present invention.

As an example of possible information stored by the monitoring means 20, FIG. 4 shows the dental tip 12 connected to the handpiece 10. When the dental tip 12 is used at a dental area 18, as shown in FIG. 2, the pressure of using the dental tip 12 will axially force it backwards towards the handpiece 10, as depicted in FIG. 4. The monitoring means 20 can be used to tell the specific force exerted on the dental tip 12, which can be used to indicate specifically the wear patterns for a particular dental tip. Particularly, the monitoring means 20 will be able to determine the force exerted on and the power amplitude applied to the dental tip 12 when it failed and whether the applied forces were within the normal operation range for the dental tip 12.

Figure 5:
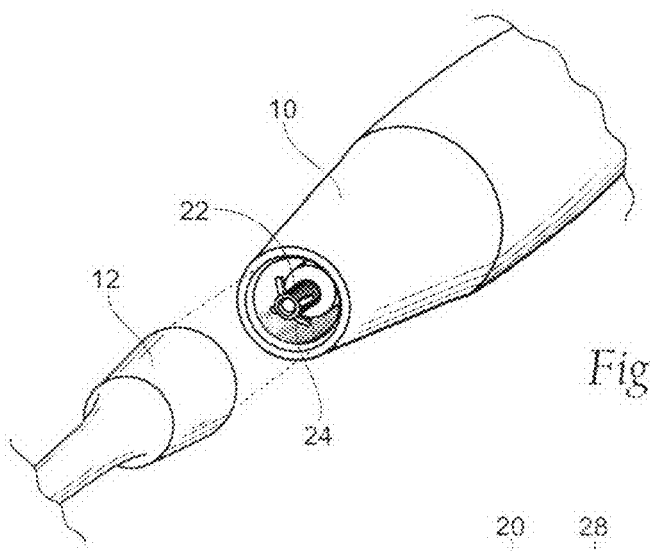
FIG. 5 is a close-up perspective view of a dental handpiece having a connection for a dental tip according to the present invention.

FIG. 5 shows up a close-up view of the connection of the handpiece 10 and the dental tip 12. The handpiece 10 houses an ultrasonic insert 22, which provides the necessary vibration to the dental tip 12. The insert 22 has a plurality of barbs or electrical connectors 24 that will provide contacts for the dental tip 12, whereby information can be submitted electronically to the base station 14. The barbs 24 could be of any known shape or arrangement used to provide an electrical connection.

Still referring to FIG. 5, the connectors 24 could also act as an electrical conduit from the handpiece 10 and/or the base station 14 for monitoring purposes, particularly for determining proper operating parameters. If, for example, the monitoring means 20 comprised a circuit breaker, the connectors would provide the necessary electrical circuitry to properly employ the circuit breaker. Preferably, the circuit breaker would be tripped if the handpiece 10 was operated at too high of a speed or frequency, thereby providing an indication of improper operation by the user.

Figure 6:
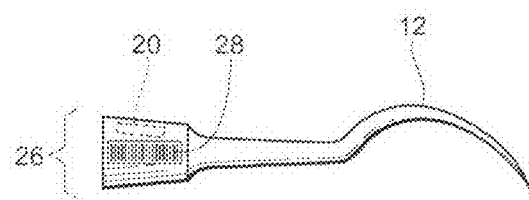
FIG. 6 is a dental tip according to the present invention, having an alternate arrangement of a monitoring device.

FIG. 6 provides the dental tip 12 having further monitoring means 26. The monitoring means comprises the microchip 20 and a bar code 28. The bar code 28 contains specific characteristics of the dental tip, such as where and when it was made, so that the dental tip 12 may be scanned to relay such information, which is constructive when determining what may have caused possible failure of the dental tip 12.

Figure 7:
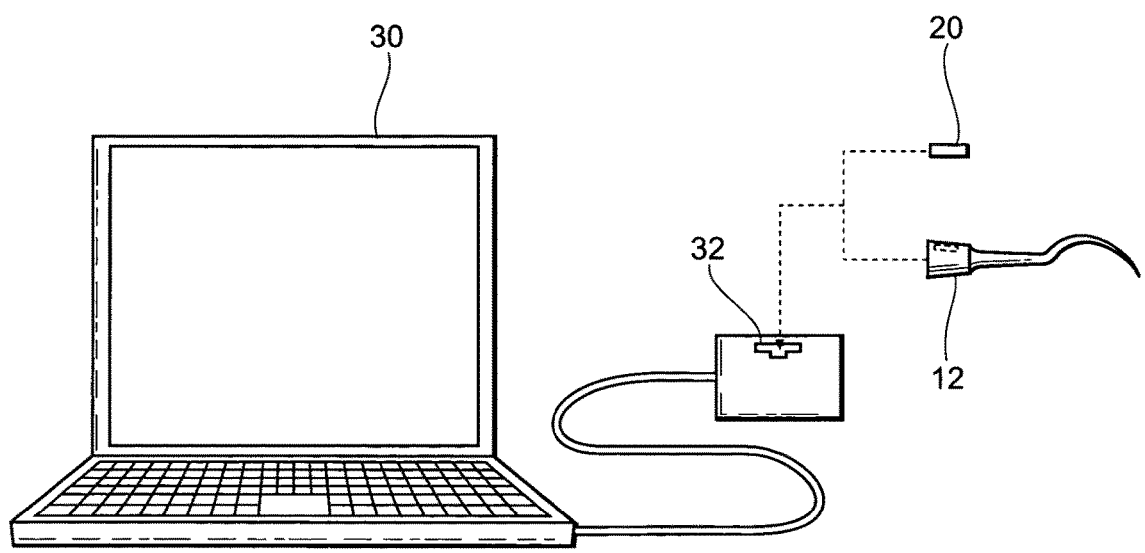
FIG. 7 is a perspective view showing a dental tip and/or a monitoring device being inserted into a device that can be used to analyze the monitoring device, such as a computer.

Along with the monitoring means 20 or 26 capability of relaying information for the user to the base station 14, the monitoring means can be used to submit information to a remote device, as depicted in FIG. 7. A computer 30 is shown having a drive or a port 32, such as USB port or similar port, that is capable of receiving the microchip 20. Alternatively, the port 32 could be designed so that the dental tip 12 would be directly attached or coupled to the port 32, which would not require removal of the microchip 20 from the dental tip 12. The monitoring means 20 or 26 also could communicate directly with the base station 14 (FIG. 1), either in a wired or wireless manner, wherein the base station 14 would further comprise the computer 30 or other processing means.

The sensing capabilities of the dental tip 12 can also be used to provide proper power settings for the handpiece 10 and the dental tip 12. For example, the bar code 28 may be read by a device, or specific information related to the dental tip 12 may be entered into the base station 14. The power setting for the dental assembly 5 could automatically be set, thereby minimizing improper wear or damage to dental tips that were operated at an improper power level or setting.

Such an advantage of monitoring the power levels of the device is useful, not only for the dentist or technician using the dental tip 12, but also for the individual supplying the dental tip 12. Dental tips generally wear over time and need to be replaced. However, sometimes the tips wear out prematurely, either by design flaws or by improper use of the tip. The present invention allows for the supplier to determine whether or not the needle has been properly used, thereby efficiently warranting the tip. For example, if a dentist or dental uses the dental tip at the wrong frequency or power setting, the means for monitoring the device would retain these characteristics, which could be then evaluated. The present invention essentially provides a "smart" tip that can store information for future use, with the monitoring means retaining the stored information for a variety of uses, including providing a warranty for the dental tip.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A piezoelectric dental device comprising:
   A base station comprising an electric power source configured to deliver power at a variable amplitude and a separate source of an electrical characteristic signal that indicates the amplitude of the power source;
   a handpiece comprising an oscillating member configured to receive power from the electric power source;
   a dental tip connectable to the handpiece and configured to operate at or below a predetermined rated amplitude upon receipt of ultrasonic vibration from the handpiece oscillating member, and
   a tip monitoring device coupled and responsive to the electrical characteristic signal so as to indicate operation of the tip above the predetermined rated amplitude without preventing operation of the dental device above the predetermined rated amplitude.

2. The dental device according to claim 1 wherein the handpiece is configured for wireless communication with the base station.

3. The dental device according to claim 1 wherein the monitoring device is removable from the dental tip.

4. The dental device according to claim 1 wherein the monitoring device is capable of communicating with an exterior device.

5. The dental device according to claim 1, wherein base station comprises the monitoring device.

6. The dental device according to claim 1, wherein the handpiece comprises the monitoring device.

7. The dental device according to claim 1, wherein dental tip comprises the monitoring device.

8. The dental device according to claim 7 wherein the monitoring device is removable from the dental tip.

9. The dental device according to claim 1, wherein the monitoring device is configured to be directly responsive to the electrical characteristic signal.

10. The dental device according to claim 1, wherein the monitoring device is configured to be indirectly responsive to the electrical characteristic signal.

11. The dental device according to claim 1, wherein the monitoring device is configured to be overloaded when the electrical characteristic signal indicates that the amplitude of the power source is above the rated power amplitude.

12. The dental device according to claim 11, wherein the monitoring device comprises a circuit breaker.

* * * * *